United States Patent [19]
Ludwig

[11] Patent Number: 5,753,101
[45] Date of Patent: May 19, 1998

[54] METHOD OF MONITORING CONSTITUENTS IN CONVERSION COATING BATHS

[76] Inventor: Frank A. Ludwig, 29443 Whitley Collins Dr., Rancho Palos Verdes, Calif. 90275

[21] Appl. No.: 690,769

[22] Filed: Aug. 1, 1996

[51] Int. Cl.⁶ ................................................. C23C 22/06
[52] U.S. Cl. ..................... 205/781; 148/241; 205/786; 205/794; 205/794.5
[58] Field of Search ........................ 205/81, 82, 83, 205/101, 794, 794.5, 780, 781, 786; 148/241; 204/402, 412, 434

[56] References Cited

U.S. PATENT DOCUMENTS

| | | | |
|---|---|---|---|
| 4,182,638 | 1/1980 | Cooke | 148/241 |
| 4,631,116 | 12/1986 | Ludwig | 205/789.5 |
| 5,298,132 | 3/1994 | Reddy et al. | 205/787 |
| 5,320,724 | 6/1994 | Ludwig et al. | 205/780.5 |
| 5,324,400 | 6/1994 | Eliash et al. | 205/794 |
| 5,336,380 | 8/1994 | Phan et al. | 205/780.5 |
| 5,391,271 | 2/1995 | Ludwig | 205/787.5 |

Primary Examiner—Kathryn L. Gorgos
Assistant Examiner—William T. Leader
Attorney, Agent, or Firm—Oppenheimer Poms Smith

[57] ABSTRACT

A method for monitoring the constituents present in conversion coating bath solutions. The method involves using specific ac and dc voltammetry and using platinum or other noble metal working electrodes. First, a selected dc potential is applied to a working electrode which has been subjected to pretreatment and which is present as an in-tank sensor in the bath being analyzed. A constant ac signal is superimposed on the dc potential. The dc potential is then swept over a chosen range at a selected sweep rate. The various constituents in the bath are then monitored by measuring dc current and the ac current at one or more reference phase angles with respect to the constant ac signal between the working electrode and a reference electrode as the dc potential is varied. The resulting dc and ac spectra provide a useful measurement of the make-up of the constituents in the bath solutions.

18 Claims, 4 Drawing Sheets

METHOD OF MONITORING CONSTITUENTS IN CONVERSION COATING BATHS

BACKGROUND OF THE INVENTION

1. Field of the Invention

The present invention relates generally to conversion coating baths and methods for monitoring the constituents contained therein. More particularly, the present invention relates to a voltammetric analysis method which is particularly suitable for rapid analysis of these baths. The method can be used to maintain desired concentrations of bath constituents to insure optimum bath performance.

2. Description of Related Art

The typical plating facility is composed of a multitude of baths for deposition of numerous coatings and metals. Many of these baths involve electroplating of metals requiring means for applying electric current to the baths to carry out the electrodeposition of metals. However most plating shops also have tanks containing baths which do not require the application of electrical current to the bath. These deposition processes include electroless plating of metals onto numerous substrates and conversion coating processes (most conversion coating processes are non-electrolytic).

An important aspect of any conversion coating process is the continual monitoring of the major and minor constituents present in the baths. Due to the electroless nature of these processes, it is necessary to monitor the baths continually to insure that the appropriate amounts of both major and minor ingredients are present. If the levels of constituents drop too low, the rate of deposition becomes uneconomical. If levels are allowed to remain too high, the conversion coating process becomes inefficient and can diminish the quality of the deposited coating.

Current major and minor constituent monitoring techniques typically involve removing a sample of the bath solution from the plating tank for subsequent wet or instrumental analysis. Typical methods of measuring major and minor constituent concentrations of various types of plating baths are disclosed in K.E. Langford and J.E. Parker, "Analysis of Electroplating and Related Solutions", pages 83–100, 65–68 and 174–180. Wet or instrumental chemical analysis methods such as these usually must be performed by highly skilled personnel. Special and costly chemical analysis equipment and supplies are required. Furthermore, the delay between drawing the samples and receiving measurement results can be anywhere from several hours to several days.

Real-time methods for measuring major and minor constituents in conversion coating processes have been developed, but are not routinely used because of high cost and inconvenience in that often the solution must be pumped out of the plating tank into equipment of substantial size and complexity. Sometimes reagent solutions are automatically mixed with the pumped solution. Usually there is no room on a plating floor for close proximity of such equipment. Also the complexity of the automatic solution mixing and preparatory analytical steps result in low reliability and high cost. In addition, and perhaps of paramount importance, is that the methods and equipment are not universal in application, and therefore cannot be used for all the various plating and conversion coating tanks in the plating shop. Methods included in these real-time, but non-universal and low practicality procedures are automatic titration, conductimetry, and specific ion and redox electrodes.

A practical, inexpensive, real-time, in-tank method for analyzing electrolytic and electroless metal plating baths which has none of the above limitations is disclosed in U.S. Pat. Nos. 4,631,116 and 5,320,724. This analytical method was and is based on the use of ac/dc voltammetric measurements. This ac/dc voltammetric analytical technique has not been applied to or otherwise used in connection with conversion coating baths or processes. The reason for this was that conversion coating baths operate on electrochemical principles which are substantially different from electrolytic and electroless baths and contain ingredients which were believed to interfere with the type of ac/dc voltammetric measurements disclosed in U.S. Pat. Nos. 4,631,116 and 5,320,724. For example, non-conductive coatings are generated during conversion coating processes. It was believed the coatings would interfere with the ac/dc voltammetric response currents.

Accordingly, there is a present need to provide a real-time, in-tank method for monitoring major and minor constituents in conversion coating baths. There is an additional need to provide a universal method and apparatus in which a single apparatus can be used to monitor bath chemistry of all the various electrolytic, electroless (including immersion deposit) and conversion coating baths which are present in many plating shops. Great advantages in terms of cost, scarcity of floor space, and equipment maintenance accrue if one apparatus located in a small room next to the shop floor can be multiplexed and connected by wires to individual sensors located in the individual plating and coating tanks on the shop floor. In this way a simple computerized apparatus could perform essentially real-time analysis for all shop tanks by a sequential multiplexing process.

SUMMARY OF THE INVENTION

In accordance with the present invention, methods are provided for monitoring constituents present in conversion coating baths. The present invention is based on the discovery that the ac/dc voltammetric monitoring methods disclosed in U.S. Pat. Nos. 4,631,116 and 5,320,724 for electrolytic plating baths and electroless metal plating baths also may be applied to conversion coating baths.

The conversion coating process, as exemplified by phosphate coating, is not included in the state of the art definition of the electroless plating process of metals. However this process is indeed "electroless" in the sense that no external current is required. It is differentiated from electroless plating in the sense that the process requires the oxidation of the metal substrate as the source of the electrons for subsequent reduction reactions. For conversion coatings, this oxidation of the metal substrate causes the reduction of hydrogen ion and the evolution of hydrogen which results in a change in pH, causing the precipitation and bonding of a phosphate or chromate salt to the metal surface. It was found that during analysis by the methods discussed in the two patents referenced above, cathodic voltages caused the evolution of hydrogen and concomitant pH changes, but these did not affect or interfere with the sensitivity, selectivity or reproducibility of these methods. Though conversion coatings precipitate at the working electrode, they do not bond to it. Neither do these precipitates diminish the analytical sensitivity, selectivity or reproducibility of the method. Therefore, even some noble metals, such as platinum or rhodium, which have low hydrogen over-voltages, can be used as sensing electrodes in these conversion coating baths. The various chemical constituents of interest in the baths can then be analyzed by employing the methods taught in the above referenced patents, particularly U.S. Pat. Nos. 4,631,116 and 5,320,724. This unexpected discovery of the lack of interference in the analysis of these baths is a basic feature of this invention.

The method of the present invention involves first applying a selected dc potential to a working electrode which has been subjected to annealing and anodic pretreatment and which is present in the bath being analyzed. A constant ac voltage is superimposed on the dc potential. The dc potential is then swept over a chosen range at a selected sweep rate. The various constituents in the bath are then monitored by measuring the ac current (at one or more reference phase angles with respect to the constant ac voltage between the working electrode and a reference electrode) as the dc potential is varied. The resulting ac spectra provides a useful measurement of the concentrations of the constituents in the various bath solutions.

The above discussed and many other features and attendant advantages of the present invention will become apparent as the invention becomes better understood by reference to the following detailed description when taken in conjunction with the accompanying drawings.

DETAILED DESCRIPTION OF THE INVENTION

As previously mentioned, a practical, inexpensive, real-time, in-tank method which has fair universality for most metal plating baths in a plating shop is disclosed in U.S. Pat. No. 4,631,116. The universality of this instrument has been augmented by succeeding patents, all assigned to Hughes Aircraft Co., Los Angeles, Calif., e.g. U.S. Pat. Nos. 5,252,192; 5,287,060; 5,296,124; 5,298,129; 5,296,123; 5,298,130; 5,298,131; 5,298,132; 5,298,145; 5,320,724. The present invention uses ac and dc voltammetric signals, generated using a common set of equipment, to provide accurate measurement spectra for major and minor constituents in conversion coating baths. In any given bath, certain voltammetric techniques may be more selective and sensitive than others for measuring a given constituent. Instead of applying separate techniques independently, the present method generates both ac and dc spectra for a bath. The method then uses the ac and dc spectra which provide the optimal spectral detail and therefore the best selectivity and sensitivity for the particular constituent concentrations. Some of the dc and ac methods involve interferences from other constituents. In order to maximize selectivity, those methods are chosen which minimize interferences. In some cases, minimization of interferences is provided by dc methods; but usually ac methods are found to be preferable.

Although the present description will focus on some exemplary voltammetric techniques, ac voltammetry as disclosed in U.S. Pat. No. 4,631,116 and specific dc voltammetry as disclosed in U.S. Pat. No. 5,320,724, it should be noted that the method of the present invention is not limited to these two techniques. The method can be used to combine any ac and dc voltammetric techniques to establish a flexible system for monitoring both major and trace constituents. Furthermore, although the following description applies the method to exemplary zinc phosphate coating baths, the present invention has wide application to many other conversion coating baths (e.g. chromate, iron phosphate, or manganese phosphate) and the constituents contained therein.

Platinum or other noble metal electrodes are preferred for their superior reproducibility. Exemplary other noble metals include gold, rhodium, iridium or alloys containing a major percentage of a noble metal. Electrodes other than the above described noble metals may be used if desired.

Figure 1:
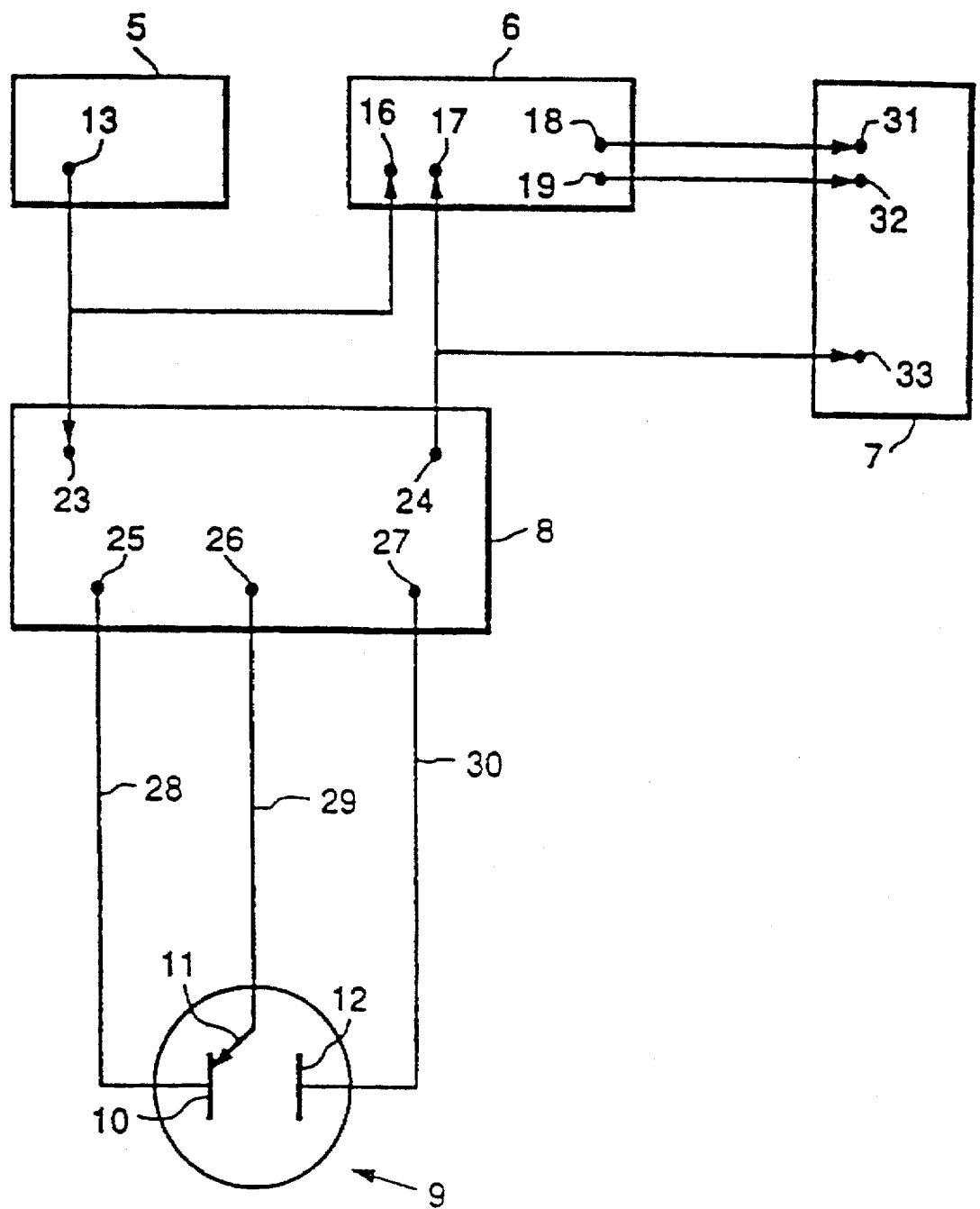
FIG. 1 is a schematic representation of a preferred exemplary system for conducting the method of the present invention.

The schematic diagram of FIG. 1 illustrates a preferred exemplary system for conducting the method of the present invention. This system is used to provide both ac and dc voltammetric signals, and is readily compatible with the equipment of U.S. Pat. No. 4,631,116 and U.S. Pat. No. 5,320,724. The contents of these patents are hereby expressly incorporated by reference. The present method thus extends the capability of the voltammetric techniques without requiring additional equipment.

In the exemplary system of FIG. 1, the conversion coating bath solution is located within an electrochemical cell 9. The electrochemical cell 9 is preferably part of an in-tank electrochemical sensor submerged within the plating bath. The solution can be drawn through the in-tank sensor by a pump. The potentiostat 8 serves to generate electrode pretreatment signals of appropriate amplitude and duration. The pretreatment signal removes any absorbed organics or other contaminants from the working electrode 10 which might interfere with ac or dc voltammetric measurements. Alternatively, the pretreatment signal could be supplied by the function or waveform generator 5. Waveform generator 5 also provides an output 13 which is an ac voltammetric signal of appropriate frequency and amplitude. The voltammetric signal is applied to the external input 23 of potentiostat 8 and as a coherent reference to the reference input 16 of a lock-in amplifier 6.

In the case of the ac voltammetric signal, the waveform generator 5 provides a constant amplitude ac signal to the external potentiostat input 23. This constant amplitude ac signal is superimposed on a sweep signal generated within potentiostat 8. Alternatively, the sweep signal could be supplied by a second external waveform generator (not shown). In some cases the voltammetric signal is simply the one generated within potentiostat 8, upon which the ac is superimposed. For ac and dc voltammetric signals, the potentiostat 8 further serves to insure that the voltammetric signal amplitude does not vary as a result of variations in current flow through the electrochemical cell 9.

The voltammetric signal output from potentiostat port 25 is then applied to the working electrode 10, a platinum wire, in the electrochemical cell 9 via line 28. The electrochemical cell 9 also contains a counter electrode 12 and a standard calomel or other reference electrode 11. The reference electrode 11 and counter electrode 12 are connected to potentiostat ports 26, 27 via lines 29, 30, respectively. The electrochemical cell 9 with electrodes 10, 11 and 12 is a sensor design typically used in conjunction with voltammetric techniques. Other sensor designs could also be used. When the ac/dc voltammetric signal is applied to the working electrode 10, a response current is generated between the working electrode 10 and the counter electrode 12. The response current signal parameters vary depending upon the electrochemical processes occurring at the surface of the working electrode 10. The electrochemical processes are a function of the constituent concentrations, and the response current is therefore responsive to these concentrations.

Both the superposed ac and dc voltammetric signal response currents are passed back through the potentiostat 8. From the potentiostat output 24 the response current is applied to the signal input 17 of lock-in amplifier 6 and to the external sweep input 33 of strip chart recorder 7 or to a computerized data acquisition system. In the case of the ac voltammetric signal response current, the lock-in amplifier serves to separate out the desired ac response current and resolve the first or second harmonic into in-phase and quadrature components. The dc voltammetric signal, however, need not be resolved into components before being displayed or computer analyzed. Certain filters are used with system 7 to filter out the ac in certain instances.

The dc or ac response current harmonic which provides the best spectral resolution is the one which should be selected for measurement. The in-phase component of the ac response current is then passed from in-phase output 18 of lock-in amplifier 6 to a display signal input 31 of system 7. Similarly, the quadrature component is passed from quadrature output 19 of lock-in amplifier 6 to a second display signal input 32 of system 7. The system 7 displays the in-phase and the quadrature components of the ac response current as a function of the dc sweep voltage. Since the dc sweep rate for a specific constituent is usually constant, the voltage axis also can be represented as a time axis. This display represents a unique ac response current spectra which is indicative of constituent concentration levels within the solution.

The dc response current is also displayed by system 7. Alternatively, a separate display means could be used for the dc response current signals. The separate display could be a stripchart recorder, a computerized digital data acquisition system, an oscilloscope or other suitable display means.

The specific equipment used in the exemplary system of FIG. 1, includes a Wavetek Model 188 waveform generator, a PAR 273 potentiostat and PAR 5210 lock-in amplifier. The Wavetek waveform generator is available from Wavetek San Diego, Inc. of San Diego, Calif. and the PAR equipment is available from Princeton Applied Research, Princeton, N.J.

In order to optimize the accuracy of the ac and dc response current spectra produced in accordance with ac and dc voltammetric techniques described above, it is necessary to vary a number of independent physical test parameters. For the ac voltammetric signals, these parameters include: 1) pretreatment signal amplitude and duration; 2) type of ac wave form (i.e., sinusoidal, square, triangular, etc.); 3) ac signal amplitude and frequency; 4) dc sweep signal voltage range and sweep rate; 5) ac response current harmonic measured, i.e. first (or fundamental), second, etc.; and 6) ac response current reference phase angle setting.

In some cases a constituent is determined by a dc voltammetric signal which is simply dc current resulting from the dc voltage sweep signal upon which the ac signal is superimposed.

In general, the dc parameters which should be varied to optimize the spectral detail for either the dc or ac response currents include: 1) pretreatment signal amplitude and duration; 2) type of dc cathodic signal wave form; 3) cathodic signal amplitude and duration; 4) type of anodic signal waveform; 5) anodic signal amplitude and duration; and 6) signal response current characteristic measured.

Values for the above ac and dc voltammetric system parameters were independently varied to determine the preferred system parameter values for monitoring constituents in accordance with the present invention. It should be emphasized that the parameter range limits described below are average and that the present invention may produce useful results with parameter values outside the specified ranges. In applying other voltammetric techniques in accordance with the method of the present invention, a similar set of parameter values applicable to these techniques would have to be optimized. Before giving exemplary values for a given zinc phosphate coating bath, a set of parameter range limits are given which are extensive enough to incorporate the more limited ranges typical for most types of conversion coating baths generally found in plating shops.

All voltages are given with respect to a saturated calomel electrode. The dc or ac response current is culled from the combined waveform. Therefore, the ranges given below apply to both the dc and ac methods. In terms of both the dc and ac voltammetric signals, the working electrode is preferably pretreated with a dc anodic potential which can vary from 0.0 volts to +3.5 volts for 2 to 30 seconds, depending on the type of bath. A sinusoidal ac waveform with an amplitude value set between 5 to 100 mv root mean square (rms) and a frequency set between about 30 to 20,000 Hz is superimposed on a dc sweep signal which is swept over an amplitude with a maximum range of about +2.0 V to −2.5 V and reversed to voltages short of or up to about +2.0 V at rates set between about 10 and 1,000 mv/sec. Optimal spectral peak resolution is obtained using the first or second harmonic of the ac response current, measured using a reference phase angle offset ranging between approximately 0 and 90 degrees. Numerous variations, including holds for brief periods at certain dc voltages, dc steps rather than sweeps to certain voltages, and several rather than just one sweep reversal may also be used.

Frequently, a constituent may produce a perturbation of the dc response current over a significant range of dc potential. However, in conversion coating baths it has been found that dc peaks usually involve significant interference from other constituents and it is best to use the fundamental or second harmonic ac signals for analysis of the constituents. A solution flow rate of zero to about 500 ml/min past the sensing electrode wire is also an important variable for both ac and dc methods. Each type of bath is unique and has a unique set of conditions for obtaining optimum analysis, with the minimum interferences from other constituents.

An example of the optimization of the exemplary ac and dc voltammetric system of FIG. 1 to detection of specific conversion coating bath constituents is as follows:

The method of the present invention was applied to a zinc phosphating bath, Bonderite 958 available from the Parker + Amchem Division of the Henkel Corp., located in Troy, Mich. A pure platinum wire was used as the sensing electrode. It was 1 mm in diameter and approximately 1 cm in length. A preliminary annealing pretreatment of the electrode has been found to be of importance for greater reproducibility of analytical results. Also, it has been found that the annealing procedure remains effective for a minimum of 8 months in some baths to over a year in other types of baths (based on daily use of the electrodes in the baths). The wire is annealed in an oxidizing flame or gas furnace at temperatures just below the melting point of platinum for about 15 seconds. It has been found that the annealing procedure is useful for all platinum sensing wires for electroless, electrolytic and immersion plating baths, and also conversion coating baths using the exemplary ac and dc voltammetric system and methods described earlier.

Most phosphate immersion and spray conversion coating processes use accelerators which maintain good phosphate coating quality by enhancing the coating deposition rate. A nitrite salt is used as accelerator in the Parker + Amchem bath. The accelerator is consumed during phosphating of substrate metals. It is the ingredient which is most profitably analyzed in a real-time mode so that timely replenishments can be made to maintain uniform bath chemistry.

Figure 2:
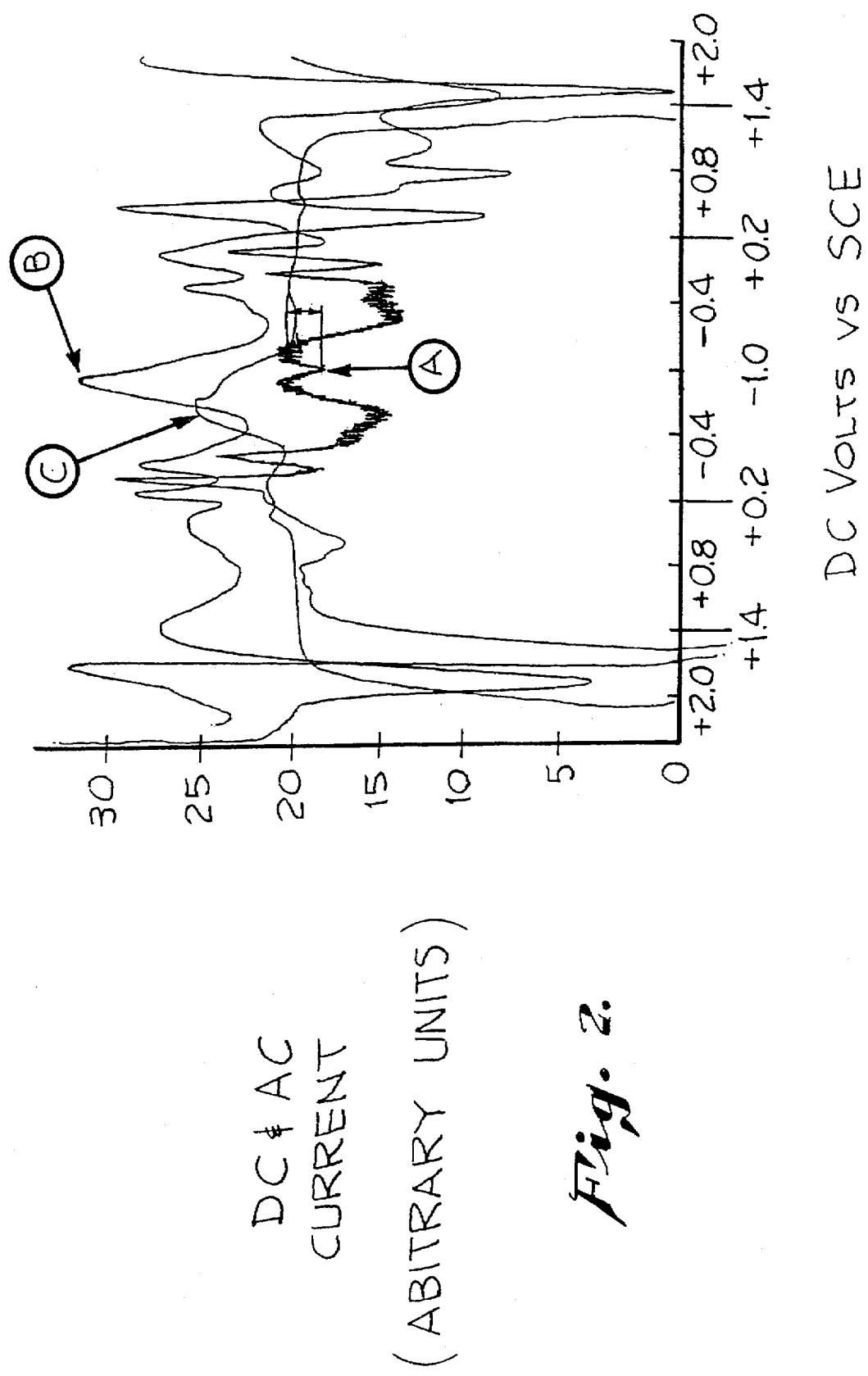
FIG. 2 is a first exemplary spectra in accordance with the present invention showing a second harmonic-in phase spectra (A), a second harmonic-quadrature spectra (B) and a DC current spectra (C). The voltage axis for the B and C spectra are offset as indicated by the vertical single-headed arrow. The voltage axis pertains to the A spectra, the A arrow is located at −1.0 V. The B and C arrows are also located at −1.0 V.
Figure 3:
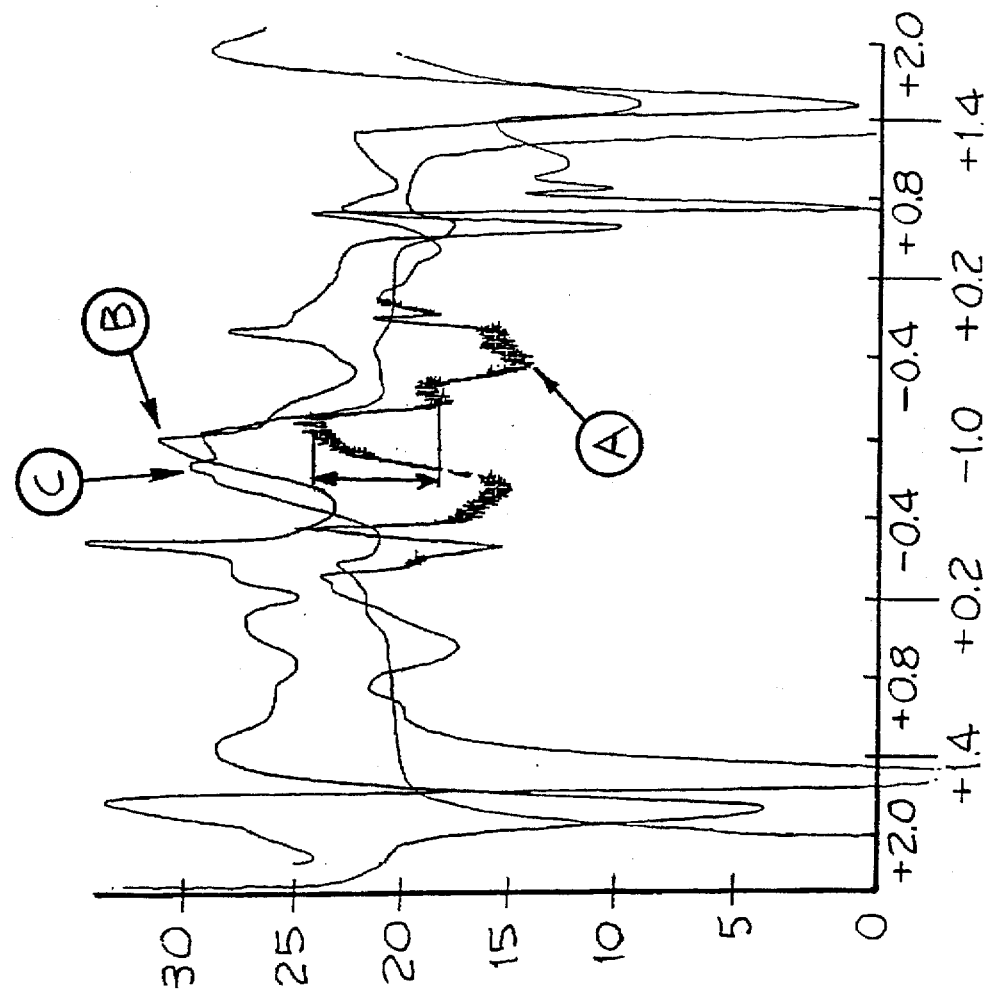
FIG. 3 is a second exemplary spectra in accordance with the present invention showing a second harmonic-in phase spectra (A), a second harmonic-quadrature spectra (B) and a DC current spectra (C). The voltage axis for the B and C spectra are offset as in FIG. 2.
Figure 4:
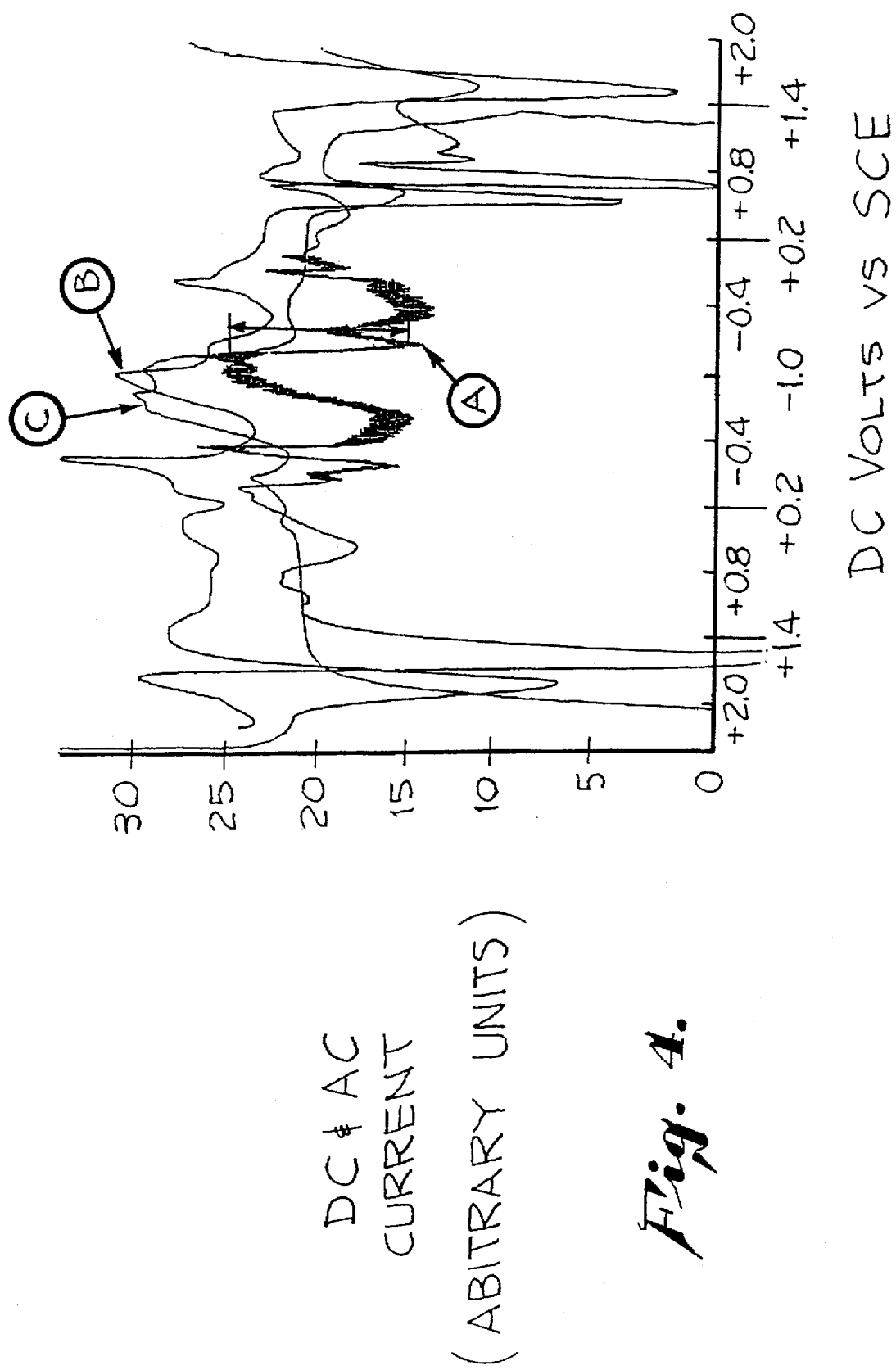
FIG. 4 is a third exemplary spectra in accordance with the present invention showing a second harmonic-in phase spectra (A), a second harmonic-quadrature spectra (B) and a DC current spectra (C). The voltage axis for the B and C spectra are offset as in FIG. 2.

Though several suitable diagnostic voltammetric peaks were found, one of the most sensitive and reproducible was an in-phase second harmonic peak based on a 500 Hz superposed 25 mv rms ac signal, with the reference phase angle set at 0°. The electrical pretreatment of the platinum sensing electrode was +2.0 V for 5 seconds followed directly by the analytical voltammetry: a dc sweep (with the aforementioned superposed ac signal) from +2.0 V to −1.0 V, and back to +2.0 V at 50 mv/sec. No solution flow was needed. The bath temperature was 45° C. A solution volume of 3.5 liters was used in a laboratory scale phosphating process of mild steel. A small peak labeled Ⓐ in FIG. 2 was obtained at −1.0 V, when no nitrite accelerator was added to the bath. This peak was enhanced on the addition of 0.5 ml accelerator solution to the 3.5 liters, and further enhanced on the addition of a second 0.5 ml. The second harmonic in-phase results are given in Table I. and displayed by the length of the two-headed arrows in FIGS. 2, 3 and 4. In FIGS. 2, 3 and 4 the Ⓐ peak shifts, but the valley stays constant at −0.9 V.

TABLE I

| BATH COMPOSITION | PEAK HEIGHT ac current (arbitrary units) |
| --- | --- |
| FIG. 2 - Zero accelerator | 4.0 |
| FIG. 3 - 0.5 ml/3.5 liters | 12.0 |
| FIG. 4 - 1.0 ml/3.5 liters | 20.0 |

Spectra Ⓑ and Ⓒ are the ac quadrature and dc spectra, respectively. In FIG. 2, the Ⓐ, Ⓑ and Ⓒ arrows are all at −1.0 V (indicating offset axes for Ⓑ and Ⓒ).

Note that the calibration is linear, with a differential of 8.0 units based on the first add, and 8.0 on the second add. Though linearity is not found in all cases in various plating (electrolytic and electroless) and coatings baths, it has been noted that linearity usually is accompanied by good reproducibility, sensitivity and minimum interferences. This applies equally to dc, fundamental and second harmonic data. It is also interesting to note that the dc data, i.e. spectra labeled Ⓒ, taken at the same time as the ac spectra gave no responsiveness to accelerator at −0.9 V where the ac data was obtained, but did show sensitivity to accelerator at +0.9 V (corrected for offset) after reversal at −1.0 V.

The corresponding dc peaks measured in the same arbitrary units were 0.7, 6.0 and 10.9. The ac did not give useful diagnostic data at +0.9 V. In this case the dc was nearly as linear as the ac. However, the ac peaks were dominant in magnitude compared to the adjacent ac spectra, whereas the dc peaks were not.

Since the sensors can be placed in the pipes or lines through which the phosphate solution is being pumped as it circulates into and out of the immersion tanks or as it is pumped to spray nozzles, the sensor and its ancillary apparatus as displayed schematically in FIG. 1 is equally useful in spray or immersion coating processes.

Also, other constituent levels of the zinc phosphate coating process can be determined by the within disclosed methods for conversion coating processes. For example, total acid and free acid levels can be of interest in maintaining optimum performance of the zinc phosphate coating process.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the above preferred embodiments, but is only limited by the following claims.

What is claimed is:

1. A method for monitoring the constituents present in a conversion coating solution used in a non-electrolytic conversion coating process wherein a conversion coating is applied to a metal substrate, said method comprising the steps of:

(a) applying a selected dc potential to a working electrode which has been subjected to annealing and anodic pretreatment, said working electrode being positioned within said solution containing said constituents, said dc potential producing a dc current; and wherein hydrogen gas is produced at said working electrode and said conversion coating precipitates at said working electrode;

(b) superimposing a constant ac voltage on said dc potential applied to said working electrode, said ac voltage having an amplitude and a frequency and producing an ac current;

(c) varying said dc potential at a chosen sweep rate over a chosen range; and (d) measuring said dc and/or said ac current or a harmonic of ac current at one or more reference phase angles with respect to said constant ac voltage between said working electrode and a reference electrode positioned within said solution as said dc potential is varied over said range, said measurement of dc and/or ac current in relation to varying dc potential being expressed as a dc and/or an ac current spectra which is used to determine and monitor said constituents in said solution.

2. A method for monitoring constituents present in a solution according to claim 1 wherein said solution is a zinc phosphate, chromate, iron phosphate, or manganese phosphate conversion coating solution.

3. A method for monitoring constituents present in a solution according to claim 2 wherein said solution is a zinc phosphate conversion coating solution.

4. A method for monitoring the constituents present in a solution according to claim 3 where the working electrode is platinum and anodic pretreatment of said working electrode comprises treating said working electrode with a dc anodic potential of about +2.0 volts for 5 seconds.

5. A method for monitoring the constituents present in a solution according to claim 1 wherein said working electrode is selected from the group of noble metals and noble metal alloys consisting of platinum, gold, indium or alloys containing a major percentage of a noble metal.

6. A method for monitoring the constituents present in a solution used in a conversion coating process according to claim 5 wherein said working electrode is platinum.

7. A method for monitoring the constituents present in a solution according to claim 5 wherein, prior to said anodic pretreatment, said noble metal or noble metal alloy of said working electrode is annealed in an oxidizing flame or gas furnace at temperatures just below the melting point of said noble metal or noble metal alloy.

8. A method for monitoring the constituents present in a solution according to claim 1 wherein said anodic pretreatment of said working electrode comprises treating said working electrode with a dc anodic potential up to +3.5 volts for 2 to 30 seconds.

9. A method for monitoring the constituents present in a solution according to claim 8 wherein said working electrode is platinum and said anodic pretreatment of said working electrode comprises treating said working electrode with a dc anodic potential of about +2.0 volts for 5 seconds.

10. A method according to claim 9 wherein said solution comprises nitrite as a constituent and said nitrite constituent is monitored, and wherein said selected dc potential applied to said working electrode is a dc sweep signal which is swept from +2.0 volts to −1.0 volt and back to +2.0 volts at a rate of 50 mv/second.

11. A method for monitoring the nitrite constituent present in a solution according to claim 10 wherein said constant ac voltage superimposed on said dc potential is a sinusoidal waveform having an amplitude of 25 mv root mean square and a frequency of 500 Hz and the second harmonic response current is measured.

12. A method for monitoring the nitrite constituent present in a solution according to claim 11 wherein said reference phase angle is 0 degrees.

13. A method for monitoring the constituents present in a solution according to claim 1 wherein said selected dc potential applied to said working electrode is a dc sweep signal which is swept over a maximum range of about +2.0 volts to −2.5 volts and reversed to voltages of up to about +2.0 volts at a rate of between about 10 to 1,000 mv/second.

14. A method for monitoring the constituents present in a solution according to claim 1 wherein said constant ac voltage superimposed upon said dc potential is a sinusoidal waveform having an amplitude of between 5 and 100 mv root mean square and a frequency of between about 30 to 20,000 Hz.

15. A method for monitoring the constituents present in a solution according to claim 1 wherein said reference phase angle is between 0 and 90 degrees.

16. A method according to claim 1 wherein said solution is a zinc phosphating solution comprising nitrite as a constituent and said nitrite constituent is monitored, and wherein said selected dc potential applied to said working electrode is a dc sweep signal which is swept from +2.0 volts to −1.0 volt and back to +2.0 volts at a rate of 50 mv/second.

17. A method according to claim 1 wherein said solution is a zinc phosphating solution comprising nitrite as a constituent and said nitrite constituent is monitored, and wherein said constant ac voltage superimposed on said dc potential is a sinusoidal waveform having an amplitude of 25 mv root mean square and a frequency of 500 Hz.

18. A method according to claim 1 wherein said solution is a zinc phosphating solution comprising nitrite as a constituent and said nitrite constituent is monitored, and wherein said ac current or a harmonic thereof is used to determine and monitor the nitrite constituent.

* * * * *